United States Patent [19]

Eckerle et al.

[11] Patent Number: 4,987,900
[45] Date of Patent: Jan. 29, 1991

[54] APPARATUS FOR POSITIONING TRANSDUCER FOR BLOOD PRESSURE MONITOR

[75] Inventors: Joseph S. Eckerle, Redwood City, Calif.; Dean C. Winter, San Antonio, Tex.

[73] Assignee: Colin Electronics Co., Ltd., Japan

[21] Appl. No.: 349,937

[22] Filed: May 3, 1989

Related U.S. Application Data

[63] Continuation of Ser. No. 41,245, Apr. 21, 1987, abandoned.

[51] Int. Cl.$^5$ .............................................. A61B 5/02
[52] U.S. Cl. ................................... 128/672; 128/677; 128/687
[58] Field of Search ................. 128/672, 677, 687–690

[56] References Cited

U.S. PATENT DOCUMENTS

| | | | |
|---|---|---|---|
| 3,102,534 | 9/1963 | Bigliano et al. | 128/672 |
| 3,154,067 | 10/1964 | Stenstrom et al. | 128/687 |
| 3,903,873 | 9/1975 | Royal et al. | 128/688 X |
| 3,926,179 | 12/1975 | Petzke et al. | 128/672 |
| 4,030,484 | 6/1977 | Kuska et al. | 128/672 |
| 4,068,654 | 1/1978 | Paavola et al. | 128/689 X |
| 4,185,621 | 6/1980 | Morrow | 128/672 |
| 4,307,727 | 12/1981 | Haynes | 128/672 |
| 4,423,738 | 1/1984 | Newgard | 128/672 |
| 4,489,731 | 12/1984 | Baumberg | 128/687 X |
| 4,561,447 | 12/1985 | Kawamura et al. | 128/687 |
| 4,867,170 | 9/1989 | Takahashi | 128/677 |

FOREIGN PATENT DOCUMENTS 2180944  4/1987  United Kingdom ............... 128/672

Primary Examiner—Max Hindenburg
Assistant Examiner—J. P. Lacyk
Attorney, Agent, or Firm—Oliff & Berridge

[57] ABSTRACT

A system for positioning a tonometric sensor array over an artery on a patient's wrist such that minimal hold down pressure is required to flatten said artery. The preferred embodiment of the invention comprises a sensor case which can be attached to a patient's wrist in a manner similar to a conventional wristwatch. A transducer piston is received in the case and is movable therein. A protrusion in the lower face of the transducer piston defines a sensor mounting platform. A sensor comprising an array of pressure sensing elements is attached to the mounting platform such that the operative face of the sensor is offset from the lower surface of the piston by a predetermined distance. The sensor platform has a shape which allows part of it to fit between the radius bone and the flexor tendon in the patient's wrist. The required hold down pressure is provided by a pressurizable bellows. Because of the dimensions of the sensor platform and the offset of the sensor, adequate flattening of the underlying artery can be achieved with a minimum hold down pressure.

9 Claims, 3 Drawing Sheets

APPARATUS FOR POSITIONING TRANSDUCER FOR BLOOD PRESSURE MONITOR

This is a continuation of co-pending application Ser. No. 07/041,245 filed on Apr. 21, 1987 now abandoned.

FIELD OF THE INVENTION

The present invention relates generally to a method and apparatus for noninvasive measurement of blood pressure through the use of pressure sensing elements. More particularly, the present invention provides an improved apparatus for mounting a sensor in a configuration which minimizes the necessary hold-down force, while ensuring maximum accuracy of the blood pressure measurement. The invention apparatus, therefore, provides improved accuracy of the measured blood pressure, while minimizing discomfort to the patient.

BACKGROUND

There has been considerable interest in recent years in the development of a monitoring system for obtaining a continuous measurement of a patient's blood pressure. One of the most promising techniques for obtaining such a continuous measurement involves the use of an arterial tonometer comprising an array of small pressure sensing elements fabricated in a silicon "chip." The use of such an array of sensor elements for blood pressure measurements is disclosed generally in U.S. Pat. No. 4,269,193 issued to Newgard and U.S. Pat. No. 4,423,738 issued to Eckerle.

In general, tonometric blood pressure measurement techniques require placement of the sensor over a superficial artery with a sufficient hold-down force to partially flatten the artery between opposing faces of the sensor and an underlying bone. In the past, the sensor was typically contained in a housing strapped to the patient's wrist such that the radial artery was beneath the sensor. At the point on the wrist where the sensor was normally attached, the radial artery passes over the radius bone and is next to the tendon of the flexor carpi radialis muscle. In prior designs, the sensor was glued to the bottom of a lead frame and its surface was flush with the bottom of a rigid metal frame, to which a flexible bellows was attached. The required hold down force was provided by internal pressure in the sensor housing above the bellows. Because the lower rim of the rigid metal frame typically rested on the radius bone and the flexor tendon, a hold down force corresponding to a pressure of greater than 200 mm of mercury inside the housing often was required to properly flatten the artery between the sensor and the underlying bone. Pressures of this magnitude can cause discomfort for the patient, especially when the measurement is taken for an extended period of time.

SUMMARY OF THE PRESENT INVENTION

In view of the difficulties associated with prior art tonometric sensors, it is an object of the present invention to provide a system for positioning a tonometric sensor array over an artery in a patient's wrist such that minimal hold down pressure is required to flatten said artery.

The preferred embodiment of the present invention comprises a sensor case which can be attached to a patient's wrist in a manner similar to a conventional wristwatch. A transducer piston is received in the case and is movable therein. The lower face of the transducer piston has a protrusion which defines a sensor mounting platform. A sensor comprising an array of pressure sensing elements is attached to the mounting platform such that the operative face of the sensor is offset from the lower surface of the piston by a predetermined distance. The sensor platform has a shape which allows part of it to fit between the radius bone and the flexor tendon in the patient's wrist. The required hold down pressure is provided by a pressurizable bellows. Because of the dimensions of the sensor platform and the offset of the sensor, adequate flattening of the underlying artery can be achieved with much lower hold down pressures than were previously possible. Using the sensor mounting arrangement of the present invention, adequate flattening of the artery can be achieved with a hold down pressure of as little as 50 mm of mercury.

DETAILED DESCRIPTION OF THE PREFERRED EMBODIMENT

Figure 1:
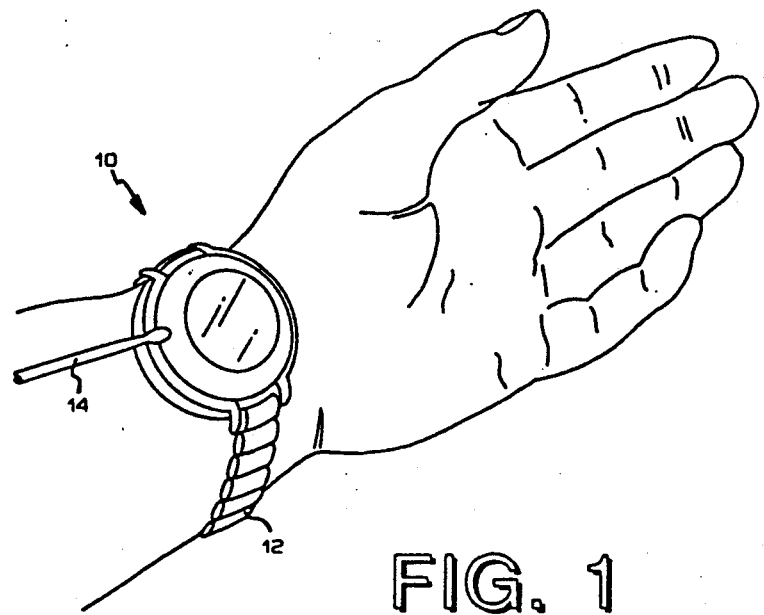
FIG. 1 is a view of the transducer housing of the present invention attached to a patient's wrist.

Referring to the drawings in more detail and to FIG. 1 in particular, the transducer housing of the present invention is shown attached to a patient's wrist. As can be seen, the housing 10 has the general appearance of an ordinary wristwatch and is secured to the patient's wrist by an adjustable band 12. A cable assembly 14 connected to the housing 10 contains electrical cables for carrying electrical signals to and from the transducer. The cable assembly 14 also contains a pneumatic tube for providing pressurized air to the interior of the housing in order to bring the sensor into contact with the patient's skin in a manner described in greater detail hereinbelow.

For the sensor in the housing to properly measure blood pressure it is important that the underlying artery be partially compressed. Specifically, it is important that the artery be flattened by a plane surface so that the stresses developed in the arterial wall perpendicular to the face of the sensor are negligible. This generally requires that the blood pressure measurement be taken on a superficial artery which runs over bone, against which the artery can be flattened.

Figure 2A:
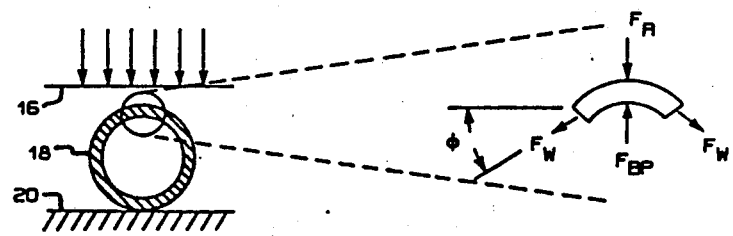
FIG. 2a is an illustration of the force balance conditions for a sensing element positioned over a superficial unflattened artery.
Figure 2B:
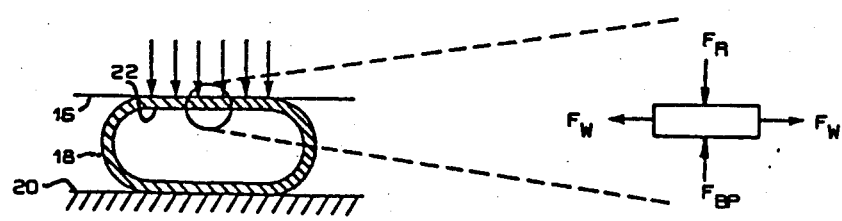
FIG. 2b is an illustration of the force balance conditions for a sensing element positioned over a superficial artery which has been partially flattened.

FIGS. 2a and 2b illustrate stresses in the wall of a superficial artery such as the radial artery of the wrist. In FIG. 2a, the force balance on a small segment of arterial wall is illustrated for an unflattened artery. In this illustration, a sensor 16 is shown exerting a compressional force against an artery 18. The artery 18 overlies a bone 20, which is illustrated with a ground symbol. In this illustration, $F_R$ represents the reaction force which is measured by the sensor; $F_W$ is the force due to stresses in the artery wall; and $F_{BP}$ is the force developed by blood pressure in the artery. The artery behaves much like an ideal membrane, supporting only tensile stresses tangent to its surface. Thus, the angle, $\phi$, of the $F_W$ vector is as shown in FIG. 2a. Specifically, $\phi$ is nonzero for an unflattened artery. This wall stress reduces the amount of stress transmitted through the tissue to the surface of the tonometer sensor. Thus, the pressure (normal stress) measured by the sensor at the skin surface is lower than the actual blood pressure. This condition can be seen by summing the Y-direction force components shown in FIG. 2a:

$$\text{Sum}(F_Y) = 0 \rightarrow F_R = F_{BP} - 2F_W \sin\phi$$

As can be seen, the force measured by the sensor is lowered by the subtractive effect of the vertical components of the wall forces.

When the artery is flattened, as shown in FIG. 2b, any stresses developed in the arterial wall are normal to the stresses transmitted to the sensor and do not affect the forces measured by the tonometer sensor. Therefore, in FIG. 2b, the force measured by one element of the tonometer sensor will be simply equal to the intra-arterial blood pressure times the area of the sensor element.

Another important criterion in a measurement of this type is that the sensor measure pressure only over that portion of the artery wall which is flattened. Typically, the underlying artery is flattened over a wider region than the size of a single sensor element. Therefore, the sensor element which happens to be placed over this narrow region where accurate blood pressure readings can be taken must be selected by parts of the tonometer control system not discussed here. This preferred measurement region is illustrated generally by reference number 22 in FIG. 2b.

In theory, it is possible to obtain an accurate measurement of blood pressure by placing a single sensor element over the narrow, flattened region of the artery described above. For accurate readings, the width of the sensor element must be less than about one fourth of the diameter of the artery. Furthermore, the sensor element must be placed over the center of the artery. Locating and maintaining a single sensor in this location is, in practice, a very difficult process.

Figure 3:
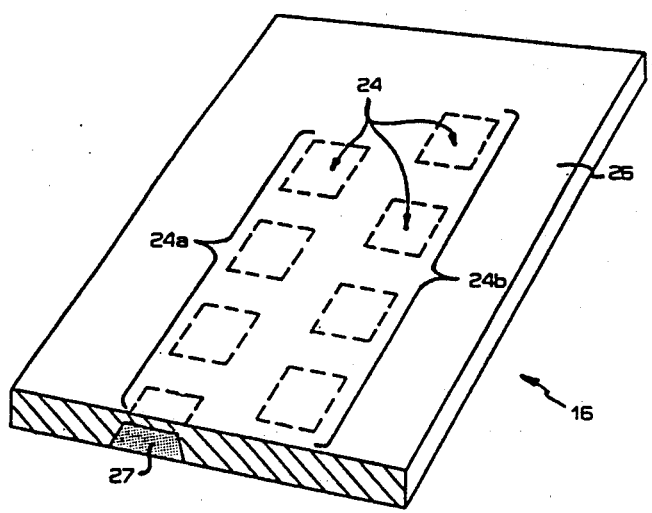
FIG. 3 is an isometric view of a sensor array of the type employed in the present invention.

To overcome the positioning difficulty described above, most arterial tonometers are based on a sensing unit 16, such as that shown in FIG. 3, comprising an array of sensor elements 24. The need for positional accuracy is partially reduced by the use of a microprocessor-based system which monitors the output of each of the individual sensing elements and chooses the element which is best located relative to the artery. A microprocessor-based system for performing this selection of sensor elements is shown generally in U.S. Pat. No. 4,423,738 issued to Newgard. Since there is a relatively large number of sensing elements 24 in the sensor array, there is a high probability that one of the sensor elements will be correctly positioned even if there is occasional movement of the sensor relative to the artery.

The array of individual sensing elements 24 may be formed in a thin rectangular monocrystalline silicon chip 26 by using modern but conventional integrated circuit fabrication techniques. Typical dimensions for such a sensor are 5 mm by 7 mm with a thickness of approximately 0.2 mm. Each of the individual sensors 24 in the illustration occupies a square area of approximately 0.50 mm × 0.50 mm. The silicon thickness in these areas is reduced by anistropic etching to a thickness of approximately 10 microns. One method which can be used to form such a silicon chip with regions of predetermined thickness in the chip is described in U.S. Pat. No. 3,888,708 issued to Wise, et al. for "Method for Forming Regions of Predetermined Thickness in Silicon."

As can be seen in FIG. 3, the array of transducer elements 24 in this case is made up of two side by side sets 24a and 24b, with each of the sets being arranged in a straight line parallel to the other set and each individual transducer element 24 of one set being offset lengthwise (along the respective longitudinal axis) so that the individual transducer elements of one set (e.g., 24a) are centered in the space between the individual transducers of the other set (e.g., 24b). The central longitudinal axis of each of the parallel sets 24a and 24b is intended to be positioned essentially perpendicular to the artery 18 where pressure is monitored. This sensor spacing configuration helps to minimize the center-to-center spacing of the individual sensor elements in the direction perpendicular to the axis of the artery. Because the individual sensor elements are so small, a number of them will overlie the artery 18. In order that the chip present a flat surface to the skin, the etched area under each individual transducer element is filled with silicone rubber 27 or some other low-modulus incompressible material.

Figure 4:
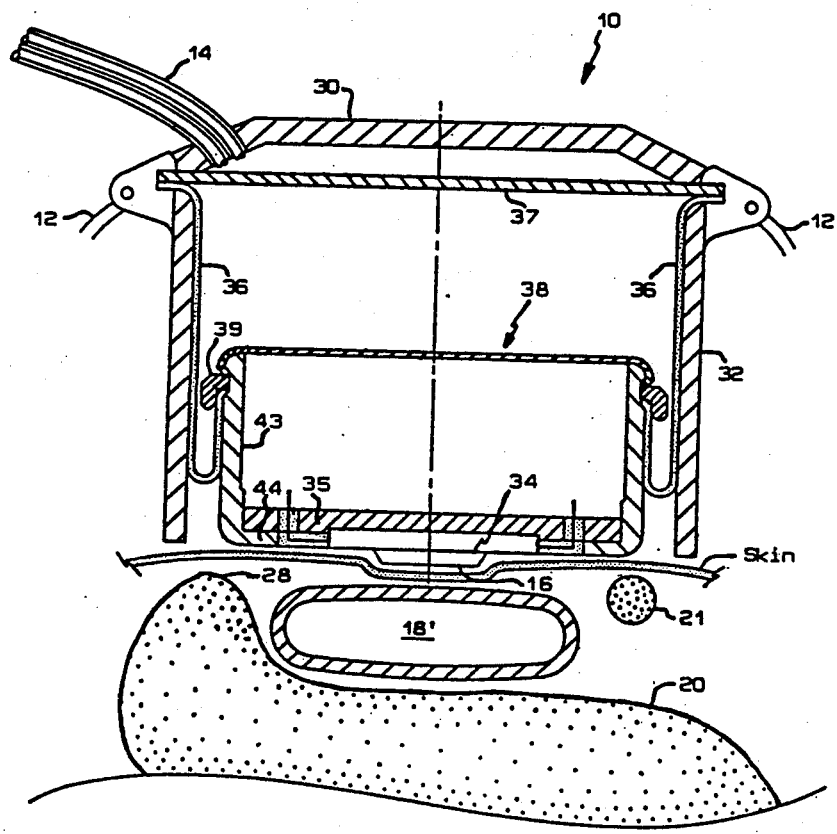
FIG. 4 is cross-sectional side view of the transducer housing of the present invention attached to a patient's wrist with the underlying radial artery properly depressed.

Referring now to FIG. 4, the transducer case 10 is a generally cylindrical, hollow container having a rigid back and side walls 30 and 32, respectively. The sensor chip 16 is mounted on a platform 34 which is attached to a support frame 35 which is further attached to the lower rim of the sidewall 43 of a cup-shaped transducer piston 38. Because of the overall shape of the platform assembly, it is sometimes referred to as a "stadium" assembly.

The transducer piston 38 is attached to the inside of the transducer case by means of a cup-like silicone rubber bellows 36. The bellows is attached to the transducer piston 38 by an annular ring 39 and is sealed to an annular ring 37 which is attached to the transducer case 10. Since the flexible rubber bellows 36 is sealed both to the transducer piston 38 and to the inside of the transducer case 10, pressurized air introduced into the interior of the case causes the operative face to be pneumatically loaded (air supply to rubber bellows not specifically illustrated), thereby keeping constant the force applied to the piston assembly. The pneumatic pressure applied inside the rubber bellows 36 may be adjusted to supply the compressional force required to provide the necessary flattening of the artery wall, thus allowing the device to meet the flattening criteria described above in connection with FIG. 2b. In the arrangement shown, the operative face of the piston assembly includes the sensor chip 16, along with its included individual transducer elements, the lower surface of the platform 34 and support frame 35, and the curved lower rim of the transducer piston sidewall 44.

When the transducer case is held in place on the wrist, generally over the radial artery, as shown in FIG.

1, and the transducer piston 38 is thus supported over the radial artery by the rubber bellows, air pressure inside the bellows holds the operative face including the sensor array 16 and its supporting structure, against the skin surface with sufficient force to achieve the desired degree of flattening of the wall of the artery. Therefore, the individual sensing elements 24 in the array each will produce an output which is directly responsive to pressure and variations in pressure on the individual element.

Referring to FIG. 4, it can be seen that a portion of the operative face of the transducer piston 38 overlies the radius bone 20 and the flexor tendon 21. In prior transducer assemblies, the sensor 16 was mounted flush in the operative face and, therefore, significant pressure was required to compress the underlying artery. This was because the operative face could not compress the artery without also displacing the tendon and exerting considerable pressure on the tissues overlying the prominence of the radius 28 shown in FIG. 4. The pressure exerted on these tissues and the flexor tendon could cause considerable discomfort for the patient.

Figure 5:
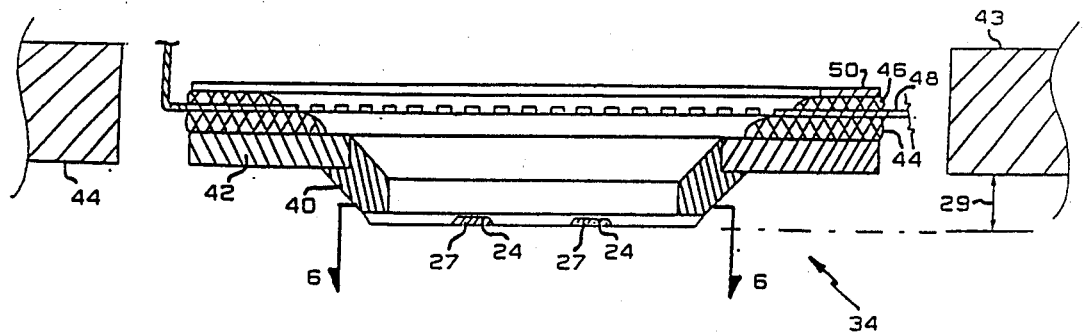
FIG. 5 is a detailed cross-sectional side view of the sensor mounting platform of the preferred embodiment.

Details relating to the improved sensor mounting arrangement of the present invention can be seen by referring to FIG. 5. The central portion of the lower face of the sensor mounting platform 34 is in the form of an inverted truncated pyramid 40, with the sensor chip 16 mounted on the lower face thereof. In the preferred embodiment, the lower rim of the pyramid 40 has a width of approximately 5 mm and a length of approximately 7 mm. The curved lower rim of the transducer piston sidewall 44 is typically flush with the top of the truncated pyramid 40, but may extend above this level. The lower circumferential rim of the piston sidewall 44 as well as layer 42 of the leadframe rests on the radius bone and the flexor tendon, as was the case in prior designs. However, because the sensor chip 16 is placed in a lower position relative to the rest of the operative face, the artery can be flattened without the previously required magnitude of hold down pressure. In the preferred embodiment of the invention, the sensor chip is offset from the rest of the operative face by approximately 2 mm. This dimension is shown by reference number 29 in FIG. 5.

The pyramid 40 is attached to a lead frame assembly comprising a plurality of alternating layers of metal and ceramic material. In the preferred embodiment, the layers 42, 48 and 50 of the lead frame are formed from a sealing alloy, such as gold plated kovar, and layers 44 and 46 are formed of a ceramic insulating material. The layer 48 includes a plurality of pads for receiving wires (not shown) which transmit the signals produced by the sensor elements 24 of the sensor array 16.

In the preferred embodiment of the present invention, the lower face of the sensor assembly is covered with a layer of silicone rubber having a thickness of approximately 0.003 inches. This layer serves both as an electrical insulator and presents a soft, nonabrasive surface to the patient's skin. This silicone rubber is also used to fill the etched areas beneath each transducer element. This filling is denoted by reference numeral 27 in FIG. 5.

Figure 6:
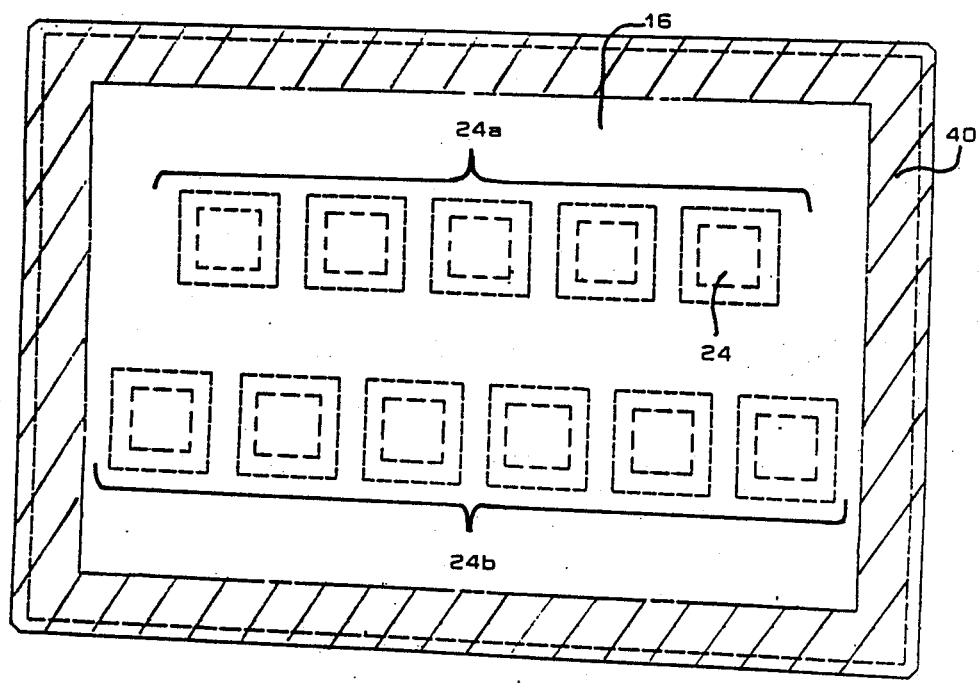
FIG. 6 is a section view, the section cut being taken along line 6—6 of FIG. 5, showing the sensor attached to the mounting platform on the lower face of the sensor piston.

FIG. 6 is a section view, the section cut being taken along lines 6—6 of FIG. 5, showing the sensor 16 mounted on the mounting platform defined by the inverted truncated pyramid 40. As was discussed above, the sensor chip 16 has a length of approximately 7 mm and a width of approximately 5 mm. Anatomical measurements have shown that the gap between the prominence of the radius bone 28 and the flexor tendon 21 lies in the range of approximately 6 mm to 12 mm for human adults. Shorter females lie near the lower end of this range and taller males near the upper end. For this reason, the length of the chip 16 in the preferred embodiment was chosen to be 7 mm, which is a compromise that gives satisfactory performance with the majority of human adults. A chip length between approximately 5 mm and 15 mm can be used for adult humans without departing from the principles of this invention. Furthermore, the size of the above-mentioned gap is considerably less in children and infants. For example, a chip length between approximately 2 mm and 6 mm would be preferred in a device intended primarily for blood pressure measurements of children. Finally, those familiar with primate anatomy would be able to choose a chip length appropriate for use on chimpanzees, orangutans, baboons, gorillas, etc.

As was discussed above, the hold down pressure required in prior art transducers is often greater than 200 mm of mercury. By contrast, using the present invention, it is often possible to obtain adequate flattening of the artery with a hold down pressure of approximately 50 mm of mercury. The present invention, therefore, provides a means for obtaining accurate measurement of blood pressure while minimizing the discomfort to the patient.

Although the method and apparatus for positioning a sensor for use with automatic blood pressure monitoring equipment of the present invention has been described in connection with the preferred embodiment, it is not intended to be limited to the specific form set forth herein, but, on the contrary, it is intended to cover such alternatives and equivalents as can reasonably be included within the spirit and scope of the invention as defined by the appended claims.

We claim

1. An apparatus for positioning a sensor over an artery of a patient to obtain a continuous measurement of the blood pressure in said artery, comprising:
   a sensor, said sensor comprising a monocrystalline silicon substrate having an array of sensing elements thereon;
   a transducer case adapted to be attached to the wrist of a patient at point where said artery overlies the radius bone and said artery lies between the prominence of said radius bone and the tendon of the flexor carpi radialis muscle;
   a piston received in said case and movable therein, said piston having a lower face engagable with the surface of the skin overlying said artery at said point on said wrist;
   a protrusion in said lower face of said piston, said protrusion defining a mounting platform to position said sensor attached thereto in a pressure-bearing relationship with the surface of the skin overlying said artery, said protrusion being offset by a predetermined distance from the lower face of said piston; and
   means for moving said piston with respect to said case to cause said sensor to bear sufficient pressure against said skin overlying said artery to be partially flattened.

2. The apparatus according to claim 1, said sensor having a width of approximately 5 millimeters and a length of approximately 7 millimeters.

3. The apparatus according to claim 2, said sensor mounting platform defined by said protrusion being offset from the lower face of said piston by approximately 2 millimeters.

4. The apparatus according to claim 3, said means for moving said piston comprising a pressurizable bellows.

5. An apparatus for positioning a sensor over an artery to obtain a continuous measurement of the blood pressure in said artery, said artery overlying a portion of the radius bone of a patient's wrist and lying between the prominence of said radius bone and the tendon of the flexor carpi radialis muscle, comprising:
- a sensor, said sensor comprising a monocrystalline silicon substrate having an array of sensing elements thereon;
- a case adapted to be secured to the wrist of said patient, said case having a piston received therein, said piston being movable with respect to said case, said piston having a lower face adapted to be engaged with the skin overlying said artery;
- a protrusion in said lower face of said piston, said protrusion defining a sensor mounting platform with said sensor being attached thereto to bear against the skin overlying said artery, said protrusion being offset from said lower face and having a width smaller than the distance between said prominence of said radius bone and said tendon to allow said sensor attached thereto to be received therebetween; and
- means for moving said piston with respect to said case to bring said sensor into pressure communication with said artery and to cause flattening thereof.

6. The apparatus according to claim 5, said sensor comprising an array of pressure sensing elements formed by etching a plurality of depressions in a piece of monocrystalline silicon.

7. The apparatus according to claim 6, said sensor having a width of approximately 5 millimeters and a length of approximately 7 millimeters.

8. The apparatus according to claim 7, said sensor mounting platform defined by said protrusion being offset from the lower face of said piston by approximately 2 millimeters.

9. The apparatus according to claim 8, said means for moving said piston comprising a pressurizable bellows.

* * * * *